United States Patent
Boykin et al.

(10) Patent No.: US 6,737,440 B2
(45) Date of Patent: May 18, 2004

(54) SYNTHESIS AND ANTIMICROBIAL ACTIVITY OF NOVEL DICATIONIC "REVERSED AMIDINES"

(75) Inventors: David W. Boykin, Atlanta, GA (US); Richard R. Tidwell, Pittsboro, NC (US); W. David Wilson, Atlanta, GA (US); John R. Perfect, Durham, NC (US); Chad F. Stephens, Villa Rica, GA (US)

(73) Assignees: The University of North Carolina at Chapel Hill, Chapel Hill, NC (US); Georgia State University Research Foundation, Inc., Atlanta, GA (US); Duke University, Durham, NC (US)

( * ) Notice: Subject to any disclaimer, the term of this patent is extended or adjusted under 35 U.S.C. 154(b) by 0 days.

(21) Appl. No.: 10/008,535

(22) Filed: Nov. 6, 2001

(65) Prior Publication Data

US 2003/0083362 A1 May 1, 2003

Related U.S. Application Data

(60) Provisional application No. 60/246,244, filed on Nov. 6, 2000.

(51) Int. Cl.⁷ .................. A61K 31/27; C07D 307/02; A61P 31/04
(52) U.S. Cl. ............... 514/491; 514/472; 549/491; 549/472
(58) Field of Search .............. 549/491, 472; 576/283.4, 176; 514/314, 471

(56) References Cited

U.S. PATENT DOCUMENTS 5,594,138 A * 1/1997 Dykstra et al. .............. 549/491
2002/0156098 A1 10/2002 Werbovetz et al. ......... 514/314

FOREIGN PATENT DOCUMENTS

WO WO02/36588 5/2002

OTHER PUBLICATIONS

Stephens, et al., *Diguanidino and "Reversed" Diamindino 2,5-Diarylfurans asn Antimicrobial Agents*, J. Med. Chem 44:1741-1748 (2001).

Kumar et al., *Palladium Catalyzed Cross–Coupling Reactions for the Synthesis of 2.5–disubstitutedfunras*, Hetercyclic Comm. 5:301–304 (1999).

Ling et al. *Models for Intramolecular Exchange in Organic π–Conjugated Open–Shell Systems: 3–Nitrenophenyl and 4–Nitrenophenyl Units Connected by 2,5–Furandiyl, 2,5–Thiophenediyl, and 2,5–Pyrrolediyl Nonalternant Exchange Linkers*, J. Am. Chem. Soc. 116:8784–8792 (1994).

Shearer et al., *S–2–Naphthylmethyl Thioacetimidate Hydrobromide: A New Odorless Reagent for the Mild Synthesis of Substituted Acetamidines*, Tetrahedron Lett. 38:179–182 (1997).

* cited by examiner

Primary Examiner—Robert W. Ramsuer
Assistant Examiner—Ebenezer Sackey
(74) Attorney, Agent, or Firm—Jenkins, Wilson & Taylor, P.A.

(57) ABSTRACT

The present invention relates to novel 2,5-bis {[alkyl(or aryl)imino]aminophenyl}furans and thiophenes of the general formula (I)

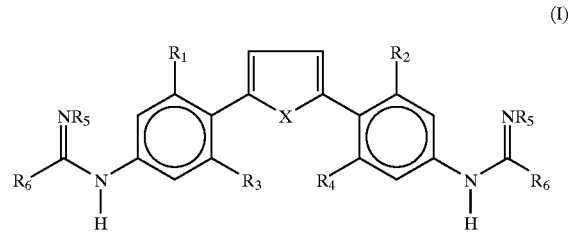

in which $R_1$, $R_2$, $R_3$ and $R_4$ are each independently selected from the group consisting of H, alkyl, alkoxy, halide, and alkylhalide groups; $R_5$ is H, alkyl or aryl; $R_6$ is H, alkyl, aryl, or $NR_7R_8$, in which $R_7$ and $R_8$ are each independently selected from the group consisting of H, alkyl and aryl; and X is O, S or $NR_9$, in which $R_9$ is H or alkyl, and to the use of such compounds.

16 Claims, 1 Drawing Sheet a) Pd(PPh₃), 1,4-dioxane, Δ. b) H₂, Pd/C, EtOAc, EtOH.
c) SnCl₂ dihydrate, EtOH, DMSO, Δ.

Legend for compounds 2-5
a $X_1$ = H, $X_2$ = H
b $X_1$ = Me, $X_2$ = H
c $X_1$ = OMe, $X_2$ = H
d $X_1$ = Cl, $X_2$ = H
e $X_1$ = CF₃, $X_2$ = H
f $X_1$ = Me, $X_2$ = Me
See Table 1 for compound 6

US 6,737,440 B2

SYNTHESIS AND ANTIMICROBIAL ACTIVITY OF NOVEL DICATIONIC "REVERSED AMIDINES"

CROSS-REFERENCE TO RELATED APPLICATIONS

The present application claims priority to U.S. Provisional Application No. 60/246,244 filed Nov. 6, 2000, the disclosure of which is incorporated herein by reference in its entirety.

STATEMENT OF GOVERNMENT SUPPORT

This invention was made with government support under grant numbers RO1AI 46365-01A2 and RO1GN61587 from the National Institutes of Health. The United States government has certain rights in this invention.

FIELD OF THE INVENTION

This invention relates to the treatment of microbial infections caused by Mycobacterium tuberculosis, Trypanosoma spp., Candida albicans, Aspergillus spp., Cryptosporidium parvum, Giardia lamblia, Plasmodium spp., Pneumocystis carinii, Toxoplasma gondii, Fusarium solani, and Cryptococcus neoformans.

BACKGROUND OF THE INVENTION

The incidence of microbial infections (e.g., mycobacterial, fungal and protozoal infections) in the immunocompromised population has significantly increased over the past several years. In particular, Candida species, especially Candida albicans, are often significant pathogens in patients infected with human immunodeficiency virus (HIV). Another pathogen, Pneumocystis carinii, causes a form of pneumonia (PCP) that is believed to be one of the leading causes of death in patients suffering from AIDS.

Human African trypanosomiasis (HAT) has reemerged as a threat to over 60 million people. Current estimates are that between 350,000 and 450,000 people are infected.

Other severe and life-threatening microbial infections are caused by Mycobacterium tuberculosis, Aspergillus spp., Cryptosporidium parvum, Giardia lamblia, Plasmodium spp., Toxoplasma gondii, Fusarium solani, and Cryptococcus neoformans.

The antimicrobial properties of dicationic molecules have been studied since the 1930's. Compounds of this type have typically utilized amidine groups as the cationic moieties, and their activities against a number of pathogens including Cryptosporidium parvum, Giardia lamblia, Leishmania spp., Plasmodium spp., Pneumocystis carinii, Toxoplasma gondii, Trypanosoma spp., Candida albicans, Aspergillus spp., and Cryptococcus neoformans have been reported. See e.g., King, H. et al., Ann. Trop. Med. Parasitol. 1938, 32,177–192; Blagburn, B. L. et al., Antimicrob. Agents Chemother. 1991, 35, 1520–1523; Bell, C. A. et al., Antimicrob. Agents Chemother. 1991, 35, 1099–1107; Bell, et al., Antimicrob. Agents Chemother. 1990, 34, 1381–1386; Kirk, R. et al., Ann. Trop. Med. Parasitol. 1940, 34, 181–197; Fulton, J. D. Ann. Trop. Med. Parasitol. 1940, 34, 53–66; Ivady, V. G. et al., Monatschr. Kinderheilkd. 1958, 106, 10–14; Boykin, D. W. et al., J. Med. Chem. 1995, 38, 912–916; Boykin, D. W. et al., J. Med. Chem. 1998, 41, 124–129; Francesconi et al., J. Med. Chem. 1999, 42, 2260–2265; Lindsay, D. S. et al., Antimicrob. Agents Chemother. 1991, 35, 1914–1916; Lourie, E. M; et al., Ann. Trop. Med. Parasitol. 1939, 33, 289–304; Lourie, E. M. et al., Ann. Trop. Med. Parasitol. 1939, 33, 305–312; Das, B. P. et al., J Med. Chem. 1976, 20, 531–536; Del Poeta, M. et al., J. Antimicrob. Chemother. 1999, 44, 223–228; Del Poeta, M. et al., Antimicrob. Agents Chemother. 1998, 42, 2495–2502; Del Poeta, M. et al., Antimicrob. Agents Chemother. 1998, 42, 2503–2510.

Despite the broad range of activity exhibited by diamidines, only one compound of this chemical type, pentamidine, has seen significant clinical use. Pentamidine has been used clinically against African trypanosomiasis, antimony-resistant leishmaniasis and P. carinii pneumonia. See e.g., Apted, F. I. C., Pharmacol. Ther. 1980, 11, 391–413; Bryceson, A. D. M. et al., Trans. Roy. Soc. Trop. Med. Hyg. 1985, 79, 705–714; Hughes, W. T.; et al., Antimicrob. Agents Chemother. 1974, 5, 289–293.

A number of compounds in this class of dicationic molecules have been shown to bind to the minor-groove of DNA at AT-rich sites and the details of their interaction with the minor-groove have been elucidated from biophysical studies and from several crystal structures. It is hypothesized that these types of molecules exert their biological activity by first binding to DNA and then by inhibiting one or more of several DNA dependent enzymes (i.e., topoisomerases, nucleases, etc.) or possibly by direct inhibition of transcription. See, Tanious, F. A. et al., J. Biomol. Struct. & Dyn. 1994, 11, 1063–1083.; Wilson, W. D. et al., J. Am. Chem. Soc. 1998, 120, 10310–10321; Bailly, C. et al., Anti-Cancer Drug Design, 1999, 14, 47–60; Mazur, et al., J. Molecular Biology 2000, 300, 321–337; Trent, J. O.; et al., J. Med. Chem. 1996, 36, 4554–4562; Guerri, A. et al., Nucleic Acids Res. 1998, 26, 2873–2878; Laughton, C. A. et al., Biochemistry 1996, 35, 5655–5661; Beerman, T. A. et al., Biochim. Biophys. Acta 1992, 1131, 52–61; Bell, C. A.; et al., Antimicrob. Agents Chemother. 1993, 37, 2668–2673; Dykstra, C. C. et al., Antimicrob. Agents Chemother. 1994, 38, 1890–1898; Hildebrandt, E. et al., J. Euk. Microbial. 1998, 45, 112–121; Henderson, D. et al., Nature Medicine 1995, 1, 525–527; Fitzgerald, D. J.; et al., J. Biol. Chem 1999, 274, 27128–27138.

2,5-Diphenylfuran and 2,4-diphenylfuran diamidines have been found to be highly effective treatments in animal models for Pneumocystis carinii and Cryptosporidium parvum. See Blagburn, B. L. et al., Antimicrob. Agents Chemother. 1991, 35, 1520–1523; Boykin, D. W. et al., J. Med. Chem. 1995, 38, 912–916; Boykin, D. W. et al.,J. Med. Chem. 1998, 41, 124–129; Francesconi, I. et al., J. Med. Chem. 1999, 42, 2260–2265; Tidwell, R. R. J. Parasitol. 1998, 84, 851–856. Furthermore, these molecules have shown antifungal activity in vitro against Candida albicans and Cryptococcus neoformans. See, Del Poeta, M. et al., J. Antimicrob. Chemother. 1999, 44, 223–228; Del Poeta, M. et al., Antimicrob. Agents Chemother. 1998, 42, 2495–2502; Del Poeta, M. et al., Antimicrob. Agents Chemother. 1998, 42, 2503–2510.

Although there are reports of antimicrobial activity of guanidino compounds, this class of cationic compounds has not been studied as extensively as their amidino analogs. See Lourie et al., Ann. Trop. Med. Parasitol. 1937, 31, 435–445.

SUMMARY OF THE INVENTION

The synthesis, DNA-binding affinities and antimicrobial properties of 2,5-bis{[alkyl(or aryl)imino] aminophenyl}furans and thiophenes are described. These compounds have the imino group of the amidine attached to an "anilino" nitrogen (in contrast to the known amidino furans in which the imino group is directly attached to the aryl ring). These compounds, hereafter, are referred to as "reversed" amidines. The various effects of placing substituents on the central phenyl rings of the 2,5-diphenylfuran framework of this class of compounds are also described.

One aspect of the invention relates to novel compounds that are useful in treating microbial infections caused by *Mycobacterium tuberculosis,* Trypanosoma spp., *Candida albicans,* Aspergillus spp., *Cryptosporidium parvum, Giardia lamblia,* Plasmodium spp., *Pneumocystis carinii, Toxoplasma gondii, Fusarium solani,* and *Cryptococcus neoformans.* Compounds of the present invention have a structure according to Formula I:

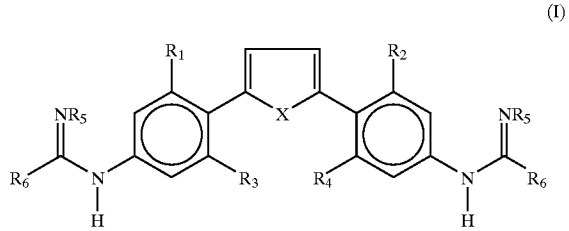

(I)

wherein:
$R_1$, $R_2$, $R_3$ and $R_4$ are each independently selected from the group consisting of H, alkyl, alkoxy, halide, and alkylhalide groups;

$R_5$ is H, alkyl or aryl;

$R_6$ is H, alkyl, aryl, or $NR_7R_8$, wherein $R_7$ and $R_8$ are each independently selected from the group consisting of H, alkyl and aryl; and X is O, S or $NR_9$, wherein $R_9$ is H or alkyl.

Additional aspects of the invention include pharmaceutical compositions comprising a compound having a structure according to Formula I, or a pharmaceutical salt thereof (i.e., an "active compound"), in a pharmaceutically acceptable carrier. Pharmaceutical compositions of the present invention are useful in the treatment of microbial infections caused by *Mycobacterium tuberculosis,* Trypanosoma spp., *Candida albicans,* Aspergillus spp., *Cryptosporidium parvum, Giardia lamblia,* Plasmodium spp., *Pneumocystis carinii, Toxoplasma gondii, Fusarium solani,* and *Cryptococcus neoformans.*

Certain aspects of the invention relate to methods of treating microbial infections caused by *Mycobacterium tuberculosis,* Trypanosoma spp., *Candida albicans,* Aspergillus spp., *Cryptosporidium parvum, Giardia lamblia,* Plasmodium spp., *Pneumocystis carinii, Toxoplasma gondii, Fusarium solani,* and *Cryptococcus neoformans,* in a subject in need of such treatment. The method comprises administering to the subject a compound according to Formulas (I), or a pharmaceutically acceptable salt thereof, in an amount effective to treat the microbial infection.

A further aspect of the present invention is the use of the active compounds described herein for the manufacture of a medicament for the treatment of microbial infections caused by *Mycobacterium tuberculosis,* Trypanosoma spp., *Candida albicans,* Aspergillus spp., *Cryptosporidium parvum, Giardia lamblia,* Plasmodium spp., *Pneumocystis carinii, Toxoplasma gondii, Fusarium solani,* and *Cryptococcus neoformans* in a subject in need of such treatment.

The foregoing and other aspects of the present invention are explained in detail in the specification set forth below.

DETAILED DESCRIPTION OF THE INVENTION

Figure 1:
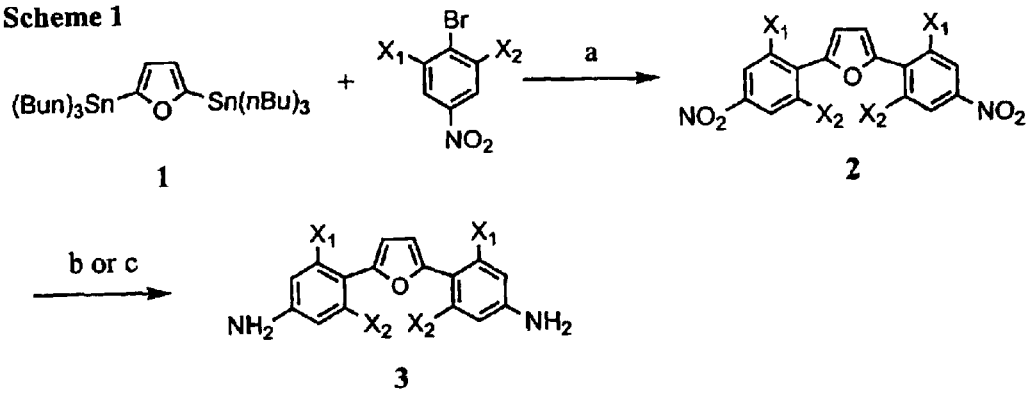
FIG. 1 illustrates various chemical schemes that may be useful in the synthesis of compounds of the present invention.
Figure 1:
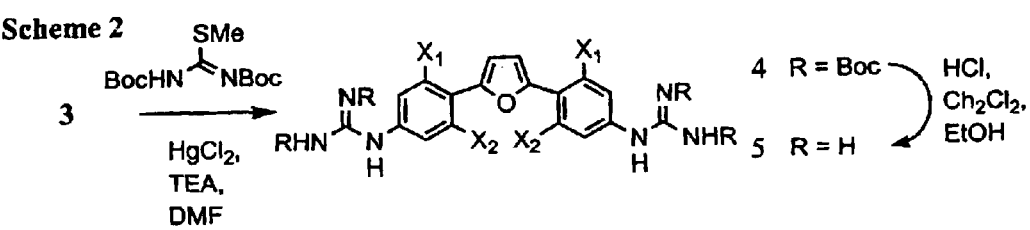
Figure 1:
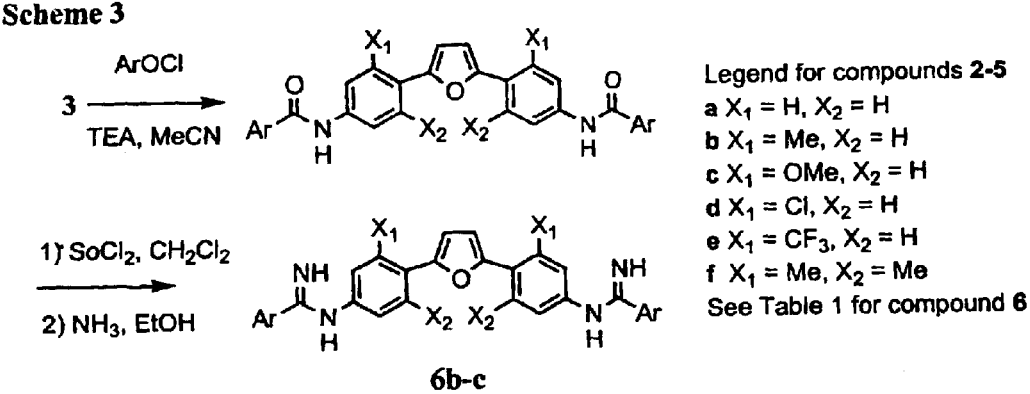
Figure 1:
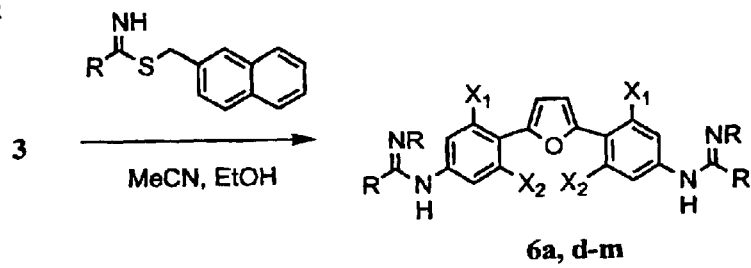

The present invention now will be described more fully hereinafter with reference to the accompanying specification and drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

With respect to the compounds of the formulas as used herein, the term "alkyl" refers to C1–10 inclusive, linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. The term "alkyl" specifically includes cycloakyl hydrocarbon chains, which as used herein refers to C3 to C6 cyclic alkyl, such as cyclopropyl, cyclobutyl, cyclopentyl, and cyclohexyl. In the present invention, preferred alkyls are the lower alkyls. The term "lower alkyl" refers to C1 to C4 linear or branched alkyl, such as methyl, ethyl, propyl, butyl, isopropyl, sec-butyl, and tert-butyl.

The term "alkyl" also encompasses substituted alkyls, which include aminoalkyls, hydroalkyls, oxygen-substituted alkyls (i.e., alkoxy groups), and halogen-substituted alkyls (i.e., alkyl halides, polyhaloalkyls). The term "aminoalkyl," as used herein, refers to C1 to C4 linear or branched amino-substituted alkyl, wherein the term "amino" refers to the group NR'R", and wherein R' and R" are independently selected from H or lower alkyl as defined above, i.e., —$NH_2$, —$NHCH_3$, —$N(CH_3)2$, etc. The term "hydroxyalkyl" as used herein refers to C1 to C4 linear or branched hydroxy-substituted alkyl, i.e., —$CH_2OH$, —$(CH_2)_2OH$, etc. The term "alkoxy" as used herein refers to C1 to C4 oxygen-substituted alkyl, i.e., —$OCH_3$. The term "loweralkoxy," as used herein, refers to C1 to C4 linear or branched alkoxy, such as methoxy, ethoxy, propyloxy, butyloxy, isopropyloxy, and t-butyloxy.

The terms "halide" has its conventional meaning and refers to fluoro, chloro, bromo, and iodo groups. Preferred halide groups include chloro groups, and preferred alkyl halides of the present invention include $CF_3$.

The term "aryl" as used herein refers to C3 to C10 cyclic aromatic groups such as phenyl, naphthyl, and the like, and specifically includes substituted aryl groups including but not limited to tolyl, substituted phenyl, and substituted naphthyl. Aryl groups may be substituted with halide, amino, nitro, and the like. Heterocyclic aromatic rings and polycyclic aromatic groups are also included in this definition of "aryl." Specific examples of aryl groups encompassed by the present invention include but are not limited to substituted and unsubstituted pyridine, quinoline, cyclopentadienyl, phenyl, furan, thiophene, pyrrole, pyran, imidazole, isothiazole, isoxazole, pyrazole, pyrazine, pyrimidine, and the like. Preferred aryl groups include pyridine, substituted pyridine (e.g., 5-methylpyridine), and quinoline.

The compounds of the present invention are also useful in the form of their pharmaceutically acceptable salt forms. Such salts may include, but are not limited to, the gluconate, lactate, acetate, tartarate, citrate, phosphate, borate, nitrate, sulfate, hydrobromide and hydrochloric salts of the compounds. Compounds of Formula (I) and their pharmaceutically acceptable salts are referred to herein as "active compounds" or "active agents."

The compounds represented by Formula (I) may be formed by synthesis procedures that are described in the Examples below, as well as by certain methods known in the art. Some of these known methods are set forth below in the Examples by description or by reference (the disclosures of which are all incorporated herein by reference in their entirety).

As noted above, the compounds, methods and compositions of the present invention are useful for treating infections caused by *Mycobacterium tuberculosis*, Trypanosoma spp., *Candida albicans*, Aspergillus spp., *Cryptosporidium parvum, Giardia lamblia,* Plasmodium spp., *Pneumocystis carinii, Toxoplasma gondii, Fusarium solani,* and *Cryptococcus neoformans*. In a preferred embodiment, the methods and compositions of the present invention are used to treat *Mycobacterium tuberculosis* infections. In another preferred embodiment, the methods and compositions of the present invention are used to treat *Candida albicans* infections. In another preferred embodiment, the methods and compositions of the present invention are used to treat infections caused by Aspergillus spp. In another preferred embodiment, the methods and compositions of the present invention are used to treat infections caused by Trypanosoma spp. The present invention is useful for treating all known species of Trypanosoma, with *Trypanosoma brucei rhodesiense* and *Trypanosoma cruzi* being particularly preferred.

Table 1. Examples of Inventive Compounds

TABLE 1

Examples of inventive compounds

| Compound Number | X | $R_1, R_2$ | Y |
|---|---|---|---|
| 5a | O | $R_1 = R_2 = H$ | NHAm |
| 6a | O | $R_1 = R_2 = H$ | NHC(=NH)-2-Pyr |
| 6b | O | $R_1 = R_2 = H$ | NHC(=NH)Ph |
| 6c | O | $R_1 = R_2 = H$ | NHC(=NH)Ph-4-$CH_3$ |
| 6d | O | $R_1 = R_2 = H$ | NHC(=NH)-c-hexane |
| 6e | O | $R_1 = R_2 = H$ | NHC(=NH)$CH_3$ |
| 6f | O | $R_1 = H, R_2 = CH_3$ | NHC(=NH)$CH_3$ |
| 5b | O | $R_1 = H, R_2 = CH_3$ | NHAm |
| 5c | O | $R_1 = H, R_2 = OCH_3$ | NHAm |
| 5d | O | $R_1 = H, R_2 = Cl$ | NHAm |

TABLE 1-continued

Examples of inventive compounds

| Compound Number | X | $R_1, R_2$ | Y |
|---|---|---|---|
| 5e | O | $R_1 = H, R_2 = CF_3$ | NHAm |
| 5f | O | $R_1 = R_2 = CH_3$ | NHAm |
| 6g | O | $R_1 = H, R_2 = CH_3$ | NHC(=NH)Ph |
| 6h | O | $R_1 = H, R_2 = CH_3$ | NHC(=NH)-2-Pyr |
| 6i | O | $R_1 = H, R_2 = CH_3$ | NHC(=NH)-2-Qu |
| 6j | O | $R_1 = H, R_2 = CH_3$ | NHC(=NH)-2-Pyr-5-$CH_3$ |
| 6k | O | $R_1 = H, R_2 = OCH_3$ | NHC(=NH)-2-Pyr |
| 6l | O | $R_1 = H, R_2 = Cl$ | NHC(=NH)-2-Pyr |
| 6m | O | $R_1 = R_2 = CH_3$ | NHC(=NH)-2-Pyr |
| DB 686 | S | $R_1 = R_2 = H$ | NHAm |
| DB 653 | S | $R_1 = R_2 = H$ | NHC(=NH)Ph |

Examples of compounds of the present invention are set forth in Table 1, in which Pyr means pyridine, c-hexane means cyclohexane, Ph means phenyl, Am means amidine, and Qu means quinoline.

In one embodiment of the invention, a subject afflicted with a microbial infection described herein is administered a therapeutically-effective amount of the compound of Formula (I), or a pharmaceutically acceptable salt thereof. A "therapeutically-effective" amount as used herein is an amount of a compound of Formula (I) that is sufficient to alleviate (e.g., mitigate, decrease, reduce) at least one of the symptoms associated with the microbial infection. It is not necessary that the administration of the compound eliminate the symptoms of the infection, as long as the benefits of administration of compound outweigh the detriments. Likewise, the terms "treat" and "treating", as used herein, are not intended to mean that the subject is necessarily cured of the microbial infection, or that all clinical signs thereof are eliminated, only that some alleviation or improvement in the condition of the subject is effected by administration of the compound of Formula (I).

Suitable subjects of the present invention include humans and animals. When the subject is an animal, mammals are preferred, with livestock and primates being particularly preferred. Humans are the most preferred subjects. Subjects may be adult, adolescent, juvenile, infant, or neonatal.

Subjects may be administered the compounds and compositions of the present invention by any suitable means. Exemplary means are oral administration (e.g., in the form of a liquid or solid), intramuscular injection, subcutaneous injection, and intravenous injection. Pharmaceutical formulations of the present invention comprise active compounds of the invention in a pharmaceutically acceptable carrier. Suitable pharmaceutical formulations include those suitable for inhalation, oral, rectal, topical, (including buccal, sublingual, dermal, vaginal and intraocular), parenteral (including subcutaneous, intradermal, intramuscular, intravenous and intraarticular) and transdernal administration. The most suitable route of administration in any given case may depend upon the anatomic location of the condition being treated in the subject, the nature and severity of the condition being treated, and the particular active compound which is being used. The formulations may conveniently be presented in unit dosage form and may be prepared by any of the methods well known in the art.

In the manufacture of a medicament according to the invention (the "formulation"), active compounds or the pharmaceutically acceptable salts thereof (the "active compounds") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 99% by weight of the active compound. One or more active compounds may be incorporated in the formulations of the invention, which formulations may be prepared by any of the well known techniques of pharmacy consisting essentially of admixing the components, optionally including one or more accessory therapeutic ingredients.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, or optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations for oral administration may optionally include enteric coatings known in the art to prevent degradation of the formulation in the stomach and provide release of the drug in the small intestine.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable, may be employed in sufficient quantity to emulsify the compound or salt in an aqueous carrier.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes produced may be reduced in size through the use of standard sonication and homogenization techniques or other techniques known in the art.

Of course, the liposomal formulations containing the pharmaceutically active compounds identified with the methods described herein may be lyophilized to produce a lyophilizate which may be reconstituted with a pharmaceutically acceptable carrier, such as water, to regenerate a liposomal suspension.

In addition to the active compounds, the pharmaceutical formulations may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use.

Pharmaceutical formulations of the present invention may comprise compounds of the present invention in lyophilized form. Alternatively, pharmaceutical formulations of the present invention may comprise compounds of the present invention in a pharmaceutically acceptable carrier. Such pharmaceutical formulations are generally made by admixing the compounds described herein with a pharmaceutically acceptable carrier. Pharmaceutically acceptable carriers are preferably liquid, particularly aqueous, carriers, the selection of which are known in the art. For the purpose of preparing such formulations, the compound may be mixed in a buffered saline (e.g., pH 6 to 8) or conventional culture media. The formulation may be stored in a sterile glass container sealed with a rubber stopper through which liquids may be injected and formulation withdrawn by syringe.

With respect to all the methods described herein, a therapeutically effective dosage of any specific compound, the use of which is in the scope of present invention, may vary somewhat from compound to compound and subject to subject, and will depend upon the condition of the subject and the route of delivery. A dosage from about 0.5 mg/kg to about 15 mg/kg of subject body weight, or about 20 mg/kg of subject body weight, or even about 25 mg/kg of subject body weight may be employed for intravenous injection or oral administration.

The concentration of the compound of the present invention or a pharmaceutically acceptable salt thereof in a formulation of the present invention may be determined by the skilled artisan and will vary according to certain conditions, including the characteristics of subject being treated (e.g., species, age, weight), the severity and type of the infecting virus or the strain that the subject is being vaccinated against, the dosage form being used, and the like.

The compounds of the present invention may be administered in conjunction with other antiviral compounds, as may be determined by the skilled artisan.

The present invention is explained in greater detail in the Examples which follow. These examples are intended as illustrative of the invention, and are not to be taken as limiting thereof.

EXAMPLE 1

General Methodology: Chemical Synthesis and Analysis

Melting points were determined with a MEL-TEMP® 3.0 capillary melting point apparatus and are uncorrected. $^1$H nuclear magnetic resonance spectra were recorded on a Varian Unity+300 or a Varian VRX 400 instrument, with peak assignments relative to residual DMSO (2.49 ppm) or $CHCl_3$ (7.24 ppm). Mass spectra were recorded on a VG Instruments 70-SE spectrometer at the Georgia Institute of Technology, Atlanta, Ga. Elemental analyses were performed by Atlantic Microlab, Norcross, Ga. All final compounds were dried in vacuo (oil pump) at 50–60° C. for at least 36 hours before elemental analysis. Unless otherwise stated, all reagent chemicals and solvents (including anhydrous solvents) were purchased from Aldrich Chemical Co., Fisher Scientific, or Lancaster Synthesis and used as received. Acetonitrile ($CaH_2$), triethylamine ($CaH_2$), and ethanol ($Mg/I_2$) were distilled from the indicated drying agent. 2,6-Dimethyl-4-nitrobromobenzene and S-(2-Naphthylmethyl) thioacetimidate were prepared according to the literature. See B. M. Wepster, *Rec. Trav. Chim.* 73, 809–818 (1954); D. N. Kravtsov, *J. Organometal. Chem.* 36, 227–237 (1972); B. G. Shearer et al., *Tetrahedron Lett.* 38, 179–182 (1997).

FIG. 1 sets forth representative schemes for the synthesis of compounds of the present invention. Although the schemes set forth in the figure relate to furan compounds, the methods illustrated therein may also be carried out with analogous compounds such as thiophene compounds. Referring to FIG. 1, the synthesis for target compounds required the corresponding diamino compounds (Scheme 1). The synthesis of the diamino compounds begins with Stille coupling between a 2,5-distannyl furan or thiophene and substituted bromonitroarenes to form the corresponding 2,5-bis[nitrophenyl]furans and thiophenes. Reduction of the 2,5-bis-nitrophenyl heterocycles either by catalytic hydrogenation or by stannous chloride produced the desired diamino compounds (Scheme 1). The required diamino analogs were obtained by the two step conversion of 2,5-bis[nitrophenyl]furans and thiophenes to amines involving Pd(0) coupling of benzophenone imine to form the corresponding arylimino compounds. The diguanidinium analogs were prepared by the reaction of the aryl diamines with Boc-protected S-methylthiourea in the presence of mercuric chloride (Scheme 2). Reaction of the aryl diamines with two equivalents of S-(2-naphthylmethyl)thiobenzimidate produced the "reversed" amidines in good yields (Scheme 4).

The 2,5-bis(4-aminophenyl)furans and -thiophenes (Scheme 1) were prepared in good yield by reduction of the corresponding bis-nitro derivatives using either catalytic hydrogenation (Pd/C), stannous chloride, or iron/AcOH. The bis-nitro derivatives, in turn, were prepared by the palladium catalyzed coupling of 2,5-bis(tri-n-butylstannyl)furan or 2,5-bis(trimethylstannyl)thiophene with the appropriate halonitrobenzene.

In the following examples, compound numbers refer to the corresponding compounds in FIG. 1.

EXAMPLE 2

Preparation of 2,5-bis(4-nitrophenyl)furans

The following representative procedures are variations of a general procedure previously described in A. Kumar et al., *Heterocyclic Comm.* 5, 301–304 (1999).

2,5-Bis(4-nitrophenyl)furan (Compound 2a). Yield: 88%; orange fluffy solid; mp 269–270° C. (not recrystallized), lit. mp 270–272° C., Ling, C. et al., *J. Am. Chem. Soc.* 1994, 116, 8784–8792.

2,5-Bis(2-methyl-4-nitrophenyl)furan (Compound 2b). To a solution of 2-bromo-5-nitrotoluene (4.32 g, 20 mmol) and tetrakis (triphenylphospine) palladium (0) (0.40 g) in anhydrous 1,4-dioxane (50 ml) was added 2,5-bis (tri-n-butylstannyl)furan (6.46 g, 10 mmol) and the mixture was heated overnight under nitrogen at 95–100° C. The resulting orange suspension was diluted with hexanes (15 ml), cooled to room-temperature, and filtered to give, after rinsing with hexanes, an orange solid (3.10 g), mp 241–243° C. The product was recrystallized from DMF (100 ml) to give a bright orange fluffy solid (2.87 g, 85%), mp 242–243° C. $^1$H NMR (DMSO-$d_6$): 2.69 (s, 6H), 7.31 (s, 2H), 8.12 (m, 4H), 8.23 (s, 2H). Anal. Calcd. for $C_{18}H_{14}N_2O_5$ (338.31): C, H, N.

2,5-Bis(2-methoxy-4-nitrophenyl)furan (Compound 2c). Yield: 77%; bright orange granular solid; mp 308–310° C. (DMF). $^1$H NMR (DMSO-$d_6$): 4.10 (s, 6H), 7.37 (s, 2H), 7.90 (s, 2H), 7.94 (d, 2H), 8.22 (d, 2H). Anal. Calcd. for $C_{18}H_{14}N_2O_7 \cdot 0.1H_2O$ (372.11): C, H, N.

2,5-Bis(2-chloro-4-nitrophenyl)furan (Compound 2d). Yield: 71%; fluffy orange solid; mp 247–247.5° C. (DMF/MeOH). $^1$H NMR (DMSO-$d_6$): 7.70 (s, 2H), 8.29 (dd, J=8.8, 2.2 Hz, 2H), 8.36 (d, J=8.8 Hz, 2H), 8.43 (d, J=2.2 Hz, 2H). Anal. Calcd. for $C_{16}H_8Cl_2N_2O_5$ (379.15): C, H, N.

2,5-Bis(4-nitro-2-trifluoromethylphenyl)furan (Compound 2e). Yield: 74%; fluffy golden needles; mp 158.5–159° C. (EtOH). $^1$H NMR (DMSO-$d_6$): 7.38 (s, 2H), 8.24 (d, J=8.7 Hz, 2H), 8.57 (d, J=2.4 Hz, 2H), 8.62 (dd, J=8.6, 2.4 Hz, 2H). Anal. Calcd. for $C_{18}H_8F_6N_2O_5$ (446.26): C, H, N.

2,5-Bis(2,6-dimethyl-4-nitrophenyl)furan (Compound 2f). Yield: 65%; yellow needles; mp 156.5–157.5° C. (DMF/EtOH/$H_2O$). $^1$H NMR (DMSO-$d_6$): 2.34 (s, 12H), 6.85 (s, 2H), 8.04 (s, 4H). Anal. Calcd. for $C_{20}H_{18}N_2O_5$ (366.36): C, H, N.

EXAMPLE 3

Preparation of 2,5-bis(4-aminophenyl)furans (The following procedures are representative)

2,5-Bis(4-aminophenyl)furan (Compound 3a). Yield: 94%; pale green/tan solid; mp 218–221° C., lit[46] mp 213–216° C. MS (EI): m/z 250 ($M^+$).

2,5-Bis(4-amino-2-methylphenyl)furan (Compound 3b). To a suspension of the bis-nitro derivative 2b (2.87 g) in EtOAc (90 ml) and dry EtOH (10 ml) was added Pd/C (10%)

(0.40 g) and the mixture was hydrogenated on a Parr apparatus at an initial pressure of ~50 psi. After the uptake of hydrogen subsided (generally 3–6 hours), the resulting solution was filtered over Celite and the pale yellow to colorless filtrate was concentrated in vacuo to near dryness to give, after dilution with hexanes, the pure diamine as a pale yellow/green solid (2.17 g, 91%), mp 174–176° C., which required no purification. $^1$H NMR (DMSO-d$_6$): 2.33 (s, 6H), 5.15 (br s, 4H), 6.42 (s, 2H), 6.46 (m, 4H), 7.35 (d, 2H). MS (EI): m/z 278 (M$^+$).

2,5-Bis(4-amino-2-methoxyphenyl)furan (Compound 3c). The original oil was reconcentrated with benzene to give a yellow/tan solid which was triturated with ether. Yield: 79%; mp 201–202.5° C. $^1$H NMR (DMSO-d$_6$): 3.80 (s, 6H), 5.25 (br s, 4H), 6.24 (dd, J=8.3, 2.0 Hz, 2H), 6.30 (d, J=1.9 Hz 2H), 6.56 (s, 2H), 7.48 (d, J=8.4 Hz, 2H). MS (EI): m/z 310 (M$^+$).

2,5-Bis(4-amino-2-chlorophenyl)furan (Compound 3d). To a suspension of the corresponding bis-nitro derivative 2d (1.22 g, 3.2 mmol) in dry EtOH (100 ml) and DMSO (20 ml) was added SnCl$_2$.2H$_2$O (5.80 g, 25.7 mmol) and the mixture was heated under nitrogen at 80° C. After 4–5 hours, TLC showed that starting material had been consumed, and thus the mixture was cooled, neutralized with NaOH (aq), and extracted with EtOAc. The extract was washed with water, brine, then dried (Na$_2$SO$_4$) and concentrated. The resulting oil was crystallized from benzene/hexane with partial concentration to give a light brown solid (0.74 g, 71%), mp 191.5–193° C. Catalytic hydrogenation was not explored. $^1$H NMR (DMSO-d$_6$): 5.60 (br s, 4H), 6.61 (dd, J=8.6, 2.2 Hz, 2H), 6.68 (d, J=2.2 Hz 2H), 6.82 (s, 2H), 7.56 (d, J=8.6 Hz, 2H). MS (EI): m/z 318 (M$^+$).

2,5-Bis(4-amino-2-trifluoromethylphenyl)furan (Compound 3e). Original red oil crystallized from EtOAc/hexanes in two crops as a red/orange solid. Combined yield: 81%; mp (first/major crop) 89.5–91° C.; mp (second crop) 91.5–92° C. $^1$H NMR (DMSO-d$_6$): 5.79 (br s, 4H), 6.52 (s, 2H), 6.82 (dd, J=8.4, 2.4 Hz, 2H), 6.98 (d, J=2.2 Hz, 2H), 7.43 (d, J=8.4 Hz, 2H). MS (EI): m/z 386 (M$^+$).

2,5-Bis(4-amino-2,6-dimethylphenyl)furan (Compound 3f). Yield: 99%; white fluffy solid; mp 144.5–146° C. $^1$H NMR (DMSO-d$_6$): 2.01 (s, 6H), 5.06 (br s, 4H), 6.24 (s, 2H), 6.29 (s, 4H). MS (EI): m/z 306 (M$^+$).

EXAMPLE 4

Preparation of 2,5-bis(4-N,N'-di-BOC-guanidinophenyl)furan derivatives (The following procedures are representative) (See Scheme 2).

2,5-Bis(4-N,N'-di-BOC guanidinophenyl)furan (Compound 4a). To a room-temperature solution of 2,5-bis (4-aminophenl)furan (0.626 g, 2.5 mmol) and 1,3-bis(tert-butoxycarbonyl)-2-methyl-2-thiopseudourea (1.56 g, 5.3 mmol) in anhydrous DMF was added triethylamine (1.59 g, 15.7 mmol) followed by mercury(II) chloride (1.57 g, 5.8 mmol) and the resulting suspension was stirred at room-temperature for 22 hours. After diluting with CH$_2$Cl$_2$ and sodium carbonate solution, the suspension was filtered over Celite and the filtrate was washed well with water (3×) and finally with brine. After drying (Na$_2$SO$_4$), the solvent was removed in vacuo and the residue was diluted with MeOH to give the BOC-protected bis-guanidine as a pale yellow solid. The collected product was purified by reprecipitation from CH$_2$Cl$_2$/MeOH to give a fluffy yellow solid (1.25 g, 68%), mp>400° C. dec. $^1$H NMR (CDCl$_3$): 1.50 and 1.53 (2s, 36H), 6.65 (s, 2H), 7.66 (s, 8H), 10.38 (br s, 2H), 11.61 (br s, 2H).

2,5-Bis(2-methyl-4-N,N'-di-BOC guanidinophenyl)furan (Compound 4b). Yellow solid, mp>250° C. dec. Yield: 62%. $^1$H NMR (CDCl$_3$): 1.51 and 1.52 (2s, 36H), 2.53 (s, 6H), 6.60 (s, 2H), 7.40 (s, 2H), 7.62 (d, 2H), 7.74 (d, 2H), 10.34 (s, 2H), 11.62 (br s, 2H).

2,5-Bis(2-methoxy-4-N,N'-di-BOC guanidinophenyl) furan (Compound 4c). Yellow solid, mp>300° C. dec. Yield: 79%. $^1$H NMR (CDCl$_3$): 1.50 and 1.53 (2s, 36H), 3.95 (s, 6H), 6.95 (s, 2H), 7.13 (d, 2H), 7.59 (s, 2H), 7.86 (d, 2H), 10.36 (s, 2H), 11.55 (br s, 2H).

2,5-Bis(2-chloro-4-N,N'-di-BOC guanidinophenyl)furan (Compound 4d). Pale yellow/tan solid, mp>400° C. dec. Yield: 63%. $^1$H NMR (CDCl$_3$): 1.52 (s, 36H), 7.17 (s, 2H), 7.63 (dd, 2H), 7.79 (d, 2H), 7.88 (d, 2H), 10.43 (s, 2H), 11.59 (br s, 2H).

2,5-Bis(2-trifluoromethyl-4-N,N'-di-BOC guanidinophenyl)furan (Compound 4e). Bright orange solid. Yield: 88%. $^1$H NMR (CDCl$_3$): 1.51 and 1.53 (2s, 36H), 6.77 (s, 2H), 7.82 (d, 2H), 7.94 (s, 2H), 8.00 (d, 2H), 10.52 (s, 2H), 11.59 (br s, 2H).

2,5-Bis(2,6-dimethyl-4-N,N'-di-BOC guanidinophenyl) furan (Compound 4f). Pale yellow/off-white solid, mp>300° C. dec. Yield: 89%. $^1$H NMR (CDCl$_3$): 1.51 and 1.53 (2s, 36H), 2.23 (s, 12H), 6.31 (s, 2H), 7.33 (s, 4H), 10.27 (s, 2H), 11.63 (br s, 2H).

EXAMPLE 5

Deprotection of N,N'-di-BOC guanidines (The following procedures are representative).

2,5-Bis(4-guanidinophenyl)furan dihydrochloride (Compound 5a). A solution of the corresponding N,N'-di-BOC guanidine (1.19 g, 1.62 mmol) in CH$_2$Cl$_2$ (15 ml) was diluted with dry EtOH (10 ml) and saturated at ice-water bath temperature with anhydrous HCl. The solution was then stirred at room-temperature for 2–3 days (drying tube), with the product slowly precipitating (shorter reaction times generally gave incomplete deprotection). The resulting suspension was concentrated to near dryness, with the solid then taken up in hot EtOH. After filtering to clarify, the solution was concentrated to near dryness to give a suspension, which was diluted with ether and collected to yield, after drying in vacuo at 50–60° C. for 2 days, the bis-guanidine dihydrochloride as an off-white/tan solid (0.66 g, quantitative), mp>300° C. dec. $^1$H NMR (DMSO-d$_6$): 7.12 (s, 2H), 7.31 (d, 4H), 7.58 (br s, 8H), 7.86 (d, 4H), 10.09 (br s, 2H). MS (FAB, thioglycerol): m/z 335.3 (MH$^+$, 100). Anal. Calcd. for C$_{18}$H$_{18}$N$_6$O.2HCl.0.25EtOH (407.30): C, H, N.

2,5-Bis(4-guanidino-2-methylphenyl)furan dihydrochloride (Compound 5b). Tan solid, mp 265–271° C. dec. $^1$H NMR (DMSO-d$_6$): 2.53 (s, 6H), 6.93 (s, 2H), 7.17 (m, 4H), 7.56 (br s, 8H), 7.82 (d, 2H), 10.06 (br s, 2H). MS (FAB, thioglycerol): m/z 363.3 (MH$^+$, 100). Anal. Calcd. for C$_{20}$H$_{22}$N$_6$O.2HCl.1.5H$_2$O.0.66EtOH (496.93): C, H, N.

2,5-Bis(4-guanidino-2-methoxyphenyl)furan dihydrochloride (Compound 5c). Light brown solid. $^1$H NMR (DMSO-d$_6$): 3.95 (s, 6H), 6.92 (dd, 2H), 6.99 (d, 2H), 7.02 (s 2H), 7.58 (br s, 8H), 7.95 (d, 2H), 10.08 (br s, 2H). MS (EI): m/z 352 (M$^+$—NH$_2$CN, 38.0), 310 (100), 267 (38.9), 251 (8.8), 155 (18.7). Anal. Calcd. for C$_{20}$H$_{22}$N$_6$O$_3$.2HCl.1.0H$_2$O.0.33EtOH (500.57): C, H, N.

2,5-Bis(2-chloro-4-guanidinophenyl)furan dihydrochloride (Compound 5d). Tan solid, mp 300–304° C. dec. $^1$H NMR (DMSO-d$_6$): 7.31 (s, 2H), 7.33 (d, 2H), 7.47 (s, 2H), 7.72 (br s, 8H), 8.04 (d, 2H). MS (DCI, ammonia): m/z 365, 363, 361 (MH$^+$—NH$_2$CN, 8, 52, 78), 323, 321, 319 (11, 66, 100). Anal. Calcd. for C$_{18}$H$_{16}$Cl$_2$N$_6$O.2HCl.0.5H$_2$O 485.21): C, H, N, Cl.

2,5-Bis (4-guanidino-2-trifluoromethylphenyl)furan dihydrochloride (Compound 5e). Orange/red solid. $^1$H NMR (DMSO-d$_6$): 6.99 (s, 2H), 7.63 (d, 2H), 7.69 (s, 2H), 7.79 (br s, 8H), 7.91 (d, 2H), 10.37 (br s, 2H). MS (CI, isobutane): m/z 471 (MH$^{+,}$ 14), 429 (100), 387 (19). Anal. Calcd. for C$_{20}$H$_{16}$F$_6$N$_6$O.2HCl.0.67H$_2$O.0.67EtOH (586.24): C, H, N.

2,5-Bis(4-guanidino-2,6-dimethylphenyl)furan dihydrochloride (Compound 5f). Off-white solid. $^1$H NMR (DMSO-d$_6$): 2.20 (s, 12H), 6.56 (s, 2H), 7.01 (s, 4H), 7.57 (br s, 8H), 10.09 (br s, 2H). MS (FAB, thioglycerol): m/z 391.2 (MH$^{+,}$ 100). Anal. Calcd. for C$_{22}$H$_{26}$N$_6$O.2HCl.0.5H$_2$O (472.41): C, H, N.

2,5-Bis[4-(benzimidoyl)aminophenyl]thiophene Free base: yellow crystalline solid, mp 284–286° C. dec (DMF/MeOH/H$_2$O). Yield: 35%. $^1$H NMR (DMSO-d$_6$): 6.41 (br s, 4NH), 6.91 (d, 4H), 7.40 (s, 2H), 7.44 (d, 6H), 7.62 (d, 4H), 7.97 (d, 4H). Hydrochloride: yellow/orange solid, mp 304–306° C. dec. $^1$H NMR (DMSO-d$_6$): 7.56 (d, 4H), 7.67 (t, 4H), 7.70 (s, 2H), 7.77 (t, 2H), 7.90 (d, 4H), 7.95 (d, 4H), 9.13 (br s, 2H), 9.94 (br s, 2H), 11.71 (br s, 2H). MS (EI): m/z 472 (M$^{+,}$ 35.1), 369 (76.8), 266 (100), 103 (49.5), 76 (14.8). Anal. Calcd. for C$_{30}$H$_{24}$N$_4$S.2HCl.0.5H$_2$O (554.52): C, 64.97; H, 4.91; N, 10.10. Found: C, 64.95; H, 4.89; N, 10.14.

2,5-Bis[2-methyl-4-(2-pyridylimino)aminophenyl]thiophene Free base: yellow crystals, mp 152–153° C. (EtOH/H$_2$O). Yield: 20%. $^1$H NMR (DMSO-d$_6$): 2.46 (s, 6H), 6.60 (br s, 4NH), 6.82 (d, 2H), 6.90 (s, 2H), 7.16 (s, 2H), 7.42 (d, 2H), 7.55 (m, 2H), 7.95 (t, 2H), 8.30 (d, 2H), 8.63 (dd, 2H). Hydrochloride: Yellow powder, mp xxx ° C. dec. $^1$H NMR (DMSO-d$_6$): 2.54 (s, 6H), 7.36 (s, 2H), 7.39 (d, 2H), 7.48 (s, 2H), 7.66 (d, 2H), 7.85 (m, 2H), 8.22 (t, 2H), 8.47 (d, 2H), 8.89 (d, 2H), 9.37 (br s, 2H), 10.12 (br s, 2H), 11.87 (br s, 2H). MS (EI):. Anal. Calcd. for C$_{30}$H$_{26}$N$_6$S.2.5HCl.1.25H$_2$O (616.30): C, 58.46; H, 5.07; N 13.64; Cl, 14.38. Found: C, 58.83; H, 4.92; N, 13.68; Cl, 14.02.

EXAMPLE 6

Preparation of Compounds 6b–6c (Scheme 3)

The original route to the reversed amidines (which was used to prepare 6b–c) is as follows.

2,5-Bis[4-(benzimidoylamino)phenyl]furan Dihydrochloride (Compound 6b) To a chilled solution of 2,5-bis(4-aminophenyl)furan (0.25 g, 1.0 mmol) in dry acetonitrile (10 ml) was added triethylamine (0.22 g, 2.1 mmol) followed dropwise by benzoyl chloride (0.30 g, 2.1 mmol) and the resulting suspension was stirred at room-temperature for 3 hours. Water (10 ml) was then added and the precipitate was collected, rinsed with water, followed by MeOH, and finally dried in vacuo to give 2,5-bis(4-benzamidophenyl)furan as a tan solid (0.44 g, 96%), mp 312–314.5° C. $^1$H NMR (DMSO-d$_6$): 6.98 (s, 2H), 7.52–7.62 (m, 6H), 7.80 (d, 4H), 7.89 (d, 4H), 7.97 (d, 4H), 10.33 (br s, 2H).

The intermediate bis(benzamide) (0.44 g, 0.96 mmol) was suspended in anhydrous dichloromethane (40 ml) and treated with freshly distilled thionyl chloride (0.68 g, 5.7 mmol) along with 2 drops of DMF and the mixture was refluxed with vigorous stirring until a solution was obtained (20 hours). The solution was then concentrated in vacuo to give a yellow solid, which was co-evaporated with dry benzene. The obtained imidoyl chloride was dissolved in anhydrous dichloromethane (40 ml) and the solution was saturated at ice/water-bath temperature with anhydrous ammonia and sealed. After stirring overnight at room-temperature, the turbid mixture was concentrated to give a yellow solid, which was triturated with 0.5N NaOH, collected, and air dried. This free-base (0.44 g, 100%) was dissolved in boiling EtOH (50 ml), filtered, and at ice-bath temperature was treated with dry HCl. After failed attempts at inducing precipitation with the addition of ether, the solution was concentrated (high vacuum) to give the dihydrochloride as an orange hygroscopic solid, mp 242–248° C. $^1$H NMR (DMSO-d$_6$): 7.26 (s, 2H), 7.58 (d, 4H), 7.67 (t, 4H), 7.78 (t, 2H), 7.95 (d, 4H), 8.03 (d, 4H), 9.12 (br s, 2H), 9.94 (br s, 2H), 11.66 (br s, 2H). MS (EI): m/z 456 (M$^{+,}$ 100), 353 (63), 250 (62), 221 (16), 130 (15), 103 (41), 76 (14), 44 (22). Anal. Calcd. for C$_{30}$H$_{24}$N$_4$O.2HCl.0.H.0.1 (C$_2$H$_5$)(545.87):C, H, N.

2,5-Bis [4-[(4-methylbenzimidoyl)amino]phenyl]furan Dihydrochloride (Compound 6c). Following the above procedure, 2,5-bis[(4-methylbenzamido)phenyl]furan was first obtained as a pale yellow solid by reaction of 2,5-bis (4-aminophenyl)furan (0.50 g, 2.0 mmol) with 4-methylbenzoyl chloride (0.65 g, 4.2 mmol). Yield: 0.96 g, 99%; mp 348–350.5° C. $^1$H NMR (DMSO-d$_6$): 2.39 (s, 6H), 6.98 (s, 2H), 7.34 (d, 4H), 7.79 (d, 4H), 7.89 (dd, 8H), 10.25 (br s, 2H).

Subsequent conversion of the bis(benzamide) to the amidine was accomplished as above, with the exception that the precipitated product following reaction with ammonia was collected by filtration and rinsed with EtOH to give the free base directly (Yield: 34%). The dihydrochloride was obtained as an orange oily solid which crystallized in vacuo, mp 227–240° C. (hygroscopic). $^1$H NMR (DMSO-d$_6$): 2.44 (s, 6H), 7.24 (s, 2H), 7.46 (d, 4H), 7.56 (d, 4H), 7.87 (d, 4H), 8.01 (d, 4H), 9.02 (br s, 2H), 9.89 (br s, 2H), 11.66 (br s 2H). MS (EI): m/z 484 (M$^{+,}$ 59), 367 (86), 250 (100), 221 (21), 130 (20), 117 (69) 90 (19), 44 (36). Anal. Calcd. for C$_{32}$H$_{28}$N$_4$O.2HCl.0.5H$_2$O (566.51): C, H, N.

EXAMPLE 7

Alternative Preparation of bis-{[alkyl(or aryl)imino]aminophenyl}furan derivatives (Scheme 4)

The following experimental is representative. In some cases, the product was purified by recrystallization.

2,5-Bis[2-methyl-4-(2-pyridylimino)aminophenyl]furan ((Compound 6h). To a solution of 2,5-bis(4-amino-2-methylphenyl)furan (0.30 g, 1.08 mmol) in dry MeCN (5 ml) was added dry EtOH (15 ml) and the solution was chilled briefly on an ice/water bath. S-(2-Naphthylmethyl) thiobenzimidate hydrobromide (0.815 g, 2.27 mmol) was then added and the mixture was stirred overnight at room-temperature. The resulting solution was concentrated to an oil, which was triturated with ether to give a yellow solid. The solid was collected, dissolved in EtOH and basified with NaOH (1N), and the free base was extracted into EtOAc. After drying (Na$_2$SO$_4$) and removing the most of the solvent, the resulting suspension was diluted with excess ether to give a fluffy yellow solid (0.36 g, 69%), mp 188–189° C., which required no purification. $^1$H NMR (DMSO-d$_6$): 2.51 (s, 6H), 6.60 (br s, 4NH), 6.77 (s, 2H), 6.87 (m, 4H), 7.55 (dd, 2H), 7.74 (d, 2H), 7.95 (m, 2H), 8.31 (d, 2H), 8.63 (d 2H).

To prepare the hydrochloride salt, the free base was suspended in EtOH (40 ml) and treated with dry HCl gas for 5–10 min at ice-bath temperature. Continued stirring of the resulting solution for 15–20 minutes gave an orange suspension which was diluted with ether (40 ml) and filtered to yield an orange powder (0.40 g), mp >180° C. dec. $^1$H NMR (DMSO-$d_6$): 2.62 (s, 6H), 7.08 (s, 2H), 7.44 (d, 2H), 7.47 (s, 2H), 7.85 (dd, 2H), 7.99 (d 2H), 8.22 (t, 2H), 8.49 (d, 2H), 8.89 (d, 2H), 9.36 (br s, 2H), 10.13 (br s, 2H), 11.88 (br s, 2H). MS (EI): m/z 486 (M$^{+,}$ 100), 382 (77.9), 278 (12.8), 104 (20.0), 78 (8.8), 43 (28.9). Anal Calcd. for $C_{30}H_{26}N_6O.3.5HCl.0.5H_2O$ (623.20): C, H, N, Cl.

2,5-Bis[4-(2-pyridylimino)aminophenyl]furan (Compound 6a) Free base: yellow crystalline solid, mp 221–223° C. (DMF/EtOH/$H_2O$). Yield: 65% $^1$H NMR (DMSO-$d_6$): 6.80 (br s, 4NH), 6.94 (s, 2H), 7.03 (d, 4H), 7.56 (m, 2H), 7.77 (d, 4H), 7.96 (m,1 2H), 8.32 (d, 2H), 8.64 (m, 2H). Hydrochloride: Orange/red powder, mp >175° C. dec. $^1$H NMR (DMSO-$d_6$): 7.26 (s, 2H), 7.58 (d, 4H), 7.85 (dd, 2H), 8.03 (d, 4H), 8.22 (t, 2H), 8.52 (d, 2H), 8.89 (d, 2H), 9.39 (br s, 2H), 10.16 (br s, 2H), 11.91 (br s, 2H). MS (EI): m/z 458 (M$^{+,}$ $^{100}$), 354 (49.1), 250 (27.6), 221 (8.9), 130 (9.4), 105 (13.6), 78 (8.6). Anal. Calcd. for $C_{28}H_{22}N_6O.3.5HCl$ (586.12): C, H, N, Cl.

2,5-Bis[4-(cyclohexylimino)aminophenyl]furan (Compound 6d) Free base: pale yellow needles, mp 242–243° C. dec (EtOAc). Yield: 17%. $^1$H NMR (DMSO-$d_6$): 1.18–1.90 (m, 20H), 2.14 (m, 2H), 5.71 (br s, 4NH), 6.82 (s, 2H), 7.63 (d, 4H). [A 41% yield of the mono-amidine/mono-amine (free base, yellow solid, mp 195–196° C.) was isolated by chromatography on silica (EtOAc-MeOH, 9:1). The insoluble nature of the reaction medium was the likely cause of the incomplete reaction.] Dihydrochloride: tan/peach solid mp 244–248° C. dec. $^1$H NMR (DMSO-$d_6$): 1.27 (m, 6H), 1.63–1.96 (m, 14H), 2.72 (m, 2H), 7.22 (s, 2H), 7.40 (d, 4H), 7.96 (d, 2H), 8.60 (br s, 2H), 9.34 (br s, 2H), 11.39 (br s, 2H). MS (FAB, thioglycerol): m/z 469.4 (MH$^{+,}$ 100). Anal. Calcd. for $C_{30}H_{38}N_4O.2HCl.0.75EtOH.0.25H_2O$ (580.60): C, H, N.

2,5-Bis[4-(benzimidoyl)amino-2-methylphenyl]furan (Compound 6g) Free base: yellow crystalline solid. Yield: 60%. $^1$H NMR (DMSO-$d_6$): 2.48 (s, 6H), 6.50 (br s, 4NH), 6.75 (s, 2H), 6.84 (s, 4H), 7.44 (m, 6H), 7.71 (d, 2H), 7.95 (d, 4H). Hydrochloride: orange/yellow hygroscopic solid. $^1$H NMR (DMSO-$d_6$): 2.61 (s, 6H), 7.03 (s, 2H), 7.38–7.44 (m, 4H), 7.63–7.68 (m, 4H), 7.75–7.80 (m, 2H), 7.94 (d, 6H). MS (EI): m/z 484 (M$^{+,}$ 100), 381 (87.2), 278 (37.9), 235 (5.4), 218 (3.1), 190 (5.5), 144 (11.1), 103 (32.8), 76 (9.3). Anal. Calcd. for $C_{32}H_{28}N_4O.2HCl.0.5H_2O.569.39$): C, H, N.

2,5-Bis[2-methyl-4-(2-quinolylimino)aminophenyl]furan (Compound 6i). Free base: orange powdery crystals, mp 168–169° C. (EtOH). Yield: 52%. $^1$H NMR (DMSO-$d_6$): 2.54 (s, 6H), 6.80 (s, 2H), 6.95 (m, 4H), 7.69 (m, 2H), 7.78 (d, 2H), 7.84 (m, 2H), 8.07 (d, 2H), 8.12 (d, 2H), 8.44 (d, 2H), 8.50 (d, 2H). Dihydrochloride: orange solid, mp >185° C. dec. $^1$H NMR (DMSO-$d_6$): 2.65 (s, 6H), 7.10 (s, 2H), 7.50 (m, 4H), 7.85 (m, 2H), 8.01 (m, 2H), 8.20 (d, 2H), 8.26 (d, 2H), 8.46 (d, 2H), 8.80 (d, 2H), 9.44 (br s, 2H), 10.21 (br s 2H), 11.98 (br s, 2H). MS (FAB, thioglycerol): m/z 587.2 (MH$^{+,}$ 100). Anal. Calcd. for $C_{38}H_{30}N_6O.2.0HCl.1.75H_2O$ (691.13): C, H, N, Cl.

2,5-Bis[2-methyl-4-(5-methyl-2-pyridylimino)aminophenyl]furan (Compound 6j). Free base: yellow crystalline solid, mp 156–158° C. (Et$_2$O/hexanes). Yield: 74%. $^1$H NMR (DMSO-$d_6$): 2.37 (s, 6H), 2.50 (s, 6H), 6.55 (br s, 4NH), 6.75 (s, 2H), 6.85 (m, 4H), 7.70–7.76 (m, 4H), 8.18 (d, 2H), 8.45 (s, 2H). Hydrochloride: orange solid, mp >175° C. dec. $^1$H NMR (DMSO-$d_6$): 2.49 (s, 6H), 2.62 (s, 6H), 7.08 (s, 2H), 7.43 (d, 2H), 7.47 (s, 2H), 7.85 (dd, 2H), 7.98 (d, 2H), 8.03 (d, 2H), 8.42 (d, 2H), 8.74 (s, 2H), 9.29 (br s, 2H), 10.07 (br s, 2H), 11.83 (br s, 2H). MS (EI): m/z 514 (M$^{+,}$ 19.2), 396 (100), 278 (34.5), 144 (8.0), 118 (33.6), 91 (13.6), 43 (22.8). Anal. Calcd. for $C_{32}H_{30}N_6O.3.25HCl.0.75H_2O$ (646.62): C, H, N, Cl.

2,5-Bis[2-methoxy-4-(2-pyridylimino)aminophenyl]furan (Compound 6k). Free base: Bright yellow crystalline solid, mp 196–197° C. (EtOAc/Et$_2$O). Yield: 75%. $^1$H NMR (DMSO-$d_6$): 3.92 (s, 6H), 6.64 and 6.67 (d, 2H and s, 2H, overlapping a broad NH signal), 6.89 (s, 2H), 7.55 (dd, 2H), 7.86 (d, 2H), 7.95 (m, 2H), 8.32 (d, 2H), 8.63 (d, 2H). Dihydrochloride: brick orange solid, mp >180° C. dec. $^1$H NMR (DMSO-$d_6$): 4.00 (s, 6H), 7.16 (s, 2H), 7.18 (d, 2H), 7.34 (s, 2H), 7.85 (dd, 2H), 8.13 (d, 2H), 8.22 (t, 2H), 8.49 (d, 2H), 8.89 (d, 2H), 9.39 (br s, 2H), 10.15 (br s, 2H), 11.89 (br s, 2H). MS (EI): m/z 518 (M$^{+,}$ 100), 414 (90.0), 371 (13.3), 310 (12.7), 267 (9.7), 155 (6.02), 104 (25.9), 77 (9.6), 43 (13.6). Anal. Calcd. for $C_{30}H_{26}N_6O.2.0HCl.2.0H_2O$ (627.51): C, H, N, Cl.

2, 5-Bis[2-chloro-4-(2-pyridylimino)aminophenyl]furan (Compound 6l). Free base: orange crystalline solid, mp 189–190° C. (EtOH). Yield: 25%. $^1$H NMR (DMSO-$d_6$): 6.85 (br s, 4NH), 7.02 (dd, 2H), 7.08 (d, 2H), 7.17 (s, 2H), 7.56 (m, 2H), 7.93–7.98 (m, 4H), 8.29 (d, 2H), 8.64 (m, 2H). Dihydrochloride: yellow/orange solid, mp >180° C. dec. $^1$H NMR (DMSO-$d_6$): 7.45 (s, 2H), 7.60 (d, 2H), 7.80 (s, 2H), 7.86 (dd, 2H), 8.23 (m, 4H), 8.50 (d, 2H), 8.90 (d, 2H), 9.54 (br s, 2H), 10.23 (br s, 2H), 11.98 (br s, 2H). MS (EI): m/z 5.30, 528, 526 (M$^+$, 13.2, 69.8, 100), 426, 424, 422 (7.9, 48, 72.4), 322, 320, 318 (2.6, 17.4, 26.6). Anal. Calcd. for $C_{28}H_{20}Cl_2N_6O.2.0HCl.1.5H_2O$ (627.35): C, H, N, Cl.

2,5-Bis[2,6-dimethyl-4-(2-pyridylimino)aminophenyl]furan (Compound 6m). Free base: pale yellow crystals, mp 206–207° C. (EtOH). Yield: 80%. $^1$H NMR (DMSO-$d_6$): 2.19 (s, 12H), 6.47 (s, 2H), 6.55 (br s, 4NH), 6.69 (s, 4H), 7.54 (m, 2H), 7.94 (m, 2H), 8.29 (d, 2H), 8.62 (d, 2H). Hydrochloride: fluffy yellow solid, mp >xxx ° C. dec. $^1$H NMR (DMSO-$d_6$): 2.28 (s, 12H), 6.68 (s, 2H), 7.28 (s, 4H), 7.84 (m, 2H), 8.21 (t, 2H), 8.48 (d, 2H), 8.88 (d, 2H), 9.37 (br s, 2H), 10.12 (br s, 2H), 11.87 (br s, 2H). MS (EI): m/z 514 (M$^{+,}$ 8.5), 410 (38.7), 306 (100), 291 (16.0), 148 (45.4), 104 (56.3), 77 (31.0). Anal. Calcd. for $C_{32}H_{30}N_6O.3.75HCl.0.5H_2O$ (660.35): C, H, N, Cl.

EXAMPLE 8

Purification of Acetamidines

The following acetamidines were purified and characterized as the HBr salt without conversion to the free base.

2,5-Bis[4-(acetimidoyl)aminophenyl]furan Dihydrobromide (Compound 6e). Fluffy tan/orange solid, mp 307–309.5° C. dec (MeOH/EtOAc). Yield: 57%. $^1$H NMR (DMSO-$d_6$, 70° C.): 2.37 (s, 6H), 7.17 (s, 2H), 7.40 (d, 4H), 7.94 (d, 4H), 8.52 (br s 2H), 9.43 (br s, 2H), 11.13 (br s, 2H). MS (FAB, thioglycerol): m/z 333.2 (MH$^+$, 100). Anal. Calcd. for $C_{20}H_{20}N_4O.2.0HBr$ (494.23): C, H, N.

2,5-Bis [4-(acetimidoyl)amino-2-methylphenyl]furan Dihydrobromide (Compound 6f). Fluffy tan/yellow solid, mp 282.5–284° C. dec (MeOH/EtOAc). Yield: 64%. $^1$H NMR (DMSO-$d_6$, 70° C.): 2.37 (s, 6H), 2.57 (s, 6H), 6.99 (s, 2H), 7.27 (d, 2H), 7.28 (s, 2H), 7.88 (d, 2H), 8.52 (br s, 2H), 9.42 (br s, 2H), 11.12 (br s, 2H). MS (FAB, thioglycerol):

EXAMPLE 9

Preparation of pyridine-2-thiocarboxamide

Adapting the general method of Taylor, a mixture of 2-cyanopyridine (7.28 g, 7.0 mmol) and thioacetamide (10.52 g, 14.0 mmol) was treated with 60 ml of HCl-saturated DMF, and the solution was stirred vigorously in an open flask on an oil bath set initially at 80° C. (the temperature gradually rising to 95° C. over the coarse of the reaction). Taylor, E. C. et al., *J. Am. Chem. Soc.* 1960, 82, 2656–2657. After 80 minutes (TLC monitoring), the resulting orange suspension was cooled, neutralized with con. NaOH/ice, and extracted with EtOAc. The extract was washed with water (3×) and then concentrated to a light brown solid which was triturated with warm water and collected. The dried product was passed over a silica gel column eluting with EtOAc:hexanes (2:1) to give, after removal of most of the solvent and dilution with hexanes, a yellow crystalline solid (6.36 g, 66%), mp 136–137° C.; lit mp 137° C.

5-Methylpyridine-2-thiocarboxamide. Prepared as above from 2-cyano-5-methylpyridine with a reaction time of 30 minutes. See Moynehan, T. M. et al., *J. Chem. Soc.* 1962, 2637–2658. Yield: 59%. Gold crystals, mp 172.5–173° C. $^1$H NMR (CDCl$_3$): 2.39 (s, 3H), 7.60 (br s, NH), 7.61 (dd, 1H), 8.31 (d, 1H), 8.57 (d, 1H), 9.42 (br s, NH).

EXAMPLE 10

Preparation of S-(2-naphthylmethyl)thioimidates

The following new S-(2-naphthylmethyl)thioimidates were prepared according to the literature by reaction of the appropriate thioamide with (2-bromomethyl)naphthalene in refluxing CHCl$_3$ (EtOH-free) for 1.5 hr. See Shearer, B. G.; et al., *Tetrahedron Lett.* 1997, 38, 179–182. After dilution with ether, the precipitated product was collected, rinsed with ether, and dried in vacuo.

S-(2-Naphthylmethyl)cyclohexanethioimidate.HBr. Yield: 91%. White solid, mp 192–192.5° C. $^1$H NMR (DMSO-d$_6$): 1.14–1.32 (m, 3H), 1.45–1.53 (m, 2H), 1.63 (d 1H), 1.76 (d, 2H), 1.87 (d, 2H), 2.84 (t, 1H), 4.73 (s, 2H), 7.53–7.56 (m, 3H), 7.89–7.97 (m, 3H), 8.01 (s, 1H).

S-(2-Naphthylmethyl)thiobenzimidate.HBr. Yield: 94%. White solid, mp 210–212° C. dec. $^1$H NMR (DMSO-d$_6$): 4.90 (s, 2H), 7.54–7.62 (m, 2H), 7.62–7.66 (m, 3H), 7.78–7.82 (m, 1H), 7.88–7.99 (m, 5H), 8.06 (s, 1H).

S-(2-Naphthylmethyl)-2-pyridylthioimidate.HBr. Yield: 58%. White fluffy solid, mp 192° C. dec. $^1$H NMR (DMSO-d$_6$): 4.80 (s, 2H), 7.53–7.57 (m, 2H), 7.59–7.62 (dd, 1H), 7.76–7.79 (m, 1H), 7.90–7.97 (m, 3H), 8.05 (s, 1H), 8.10–8.14 (m, 1H), 8.26 (d 1H), 8.78–8.80 (m, 1H).

S-(2-Naphthylmethyl)-5-methyl-2-pyridylthioimidate.HBr. Yield: 65%. White fluffy solid, mp 190–191® C. dec. $^1$H NMR (DMSO-d6): 2.42 (s, 3H), 4.79 (s, 2H), 7.53–7.57 (m, 2H), 7.59–7.62 (dd, 1H), 7.90–7.97 (m, 4H), 8.05 (s, 1H), 8.17 (d, 1H), 8.64 (s, 1H).

S-(2-Naphthylmethyl)-2-quinolylthioimidate.HBr. Yield: 23%. Light tan fluffy solid, mp 184–186° C. dec. $^1$H NMR (DMSO-d$_6$): 4.73 (s, 2H), 7.53–7.55 (m, 2H), 7.62–7.64 (dd, 1H), 7.78 (t, 1H), 7.87–7.97 (m, 4H), 8.07 (s, 1H), 8.12 (d, 2H), 8.28 (d, 1H), 8.66 (d, 1H).

EXAMPLE 11

Biological Testing of Inventive Compounds: Materials and Methods

Differences in thermal melting values (ΔTm) were determined and DNA samples were prepared as previously described in Boykin, D. W. et al., *J Med. Chem.* 1998, 41, 124–129 and Francesconi, I. et al., *J. Med. Chem.* 1999, 42, 2260–2265.

*Mycobacterium tuberculosis* susceptibility testing. The compounds of the present invention were tested against *M. tuberculosis* H37Rv in BACTEC 12B medium using a fluorometric broth microdilution assay, the Microplate Alamar Blue Assay (MABA), according to Collins, L. et al., *Antimicrob. Agents Chemother.* 1997, 41, 1004–1009. Compounds were initially assessed at 6.25 ug/ml and those effecting a reduction in fluorescence of at least 90% relative to untreated cultures were further evaluated for MIC by testing at lower concentrations. The MIC was defined as the lowest concentration of compound effecting a reduction of ≧90% of the relative fluorescence units relative to a control culture. Antimycobacterial data were provided by the Tuberculosis Antimicrobial Acquisition and Coordinating Facility (TAACF)) through a research and development contract with the U.S. National Institute of Allergy and Infectious Diseases.

Antifungal Test organisms. The fungi used in this study for all the compounds in Table 1 included two reference strains *C. albicans* A39 and *Aspergillus fumigatus* (strain 168.95). Expanded studies on 6j employed the fungi listed in Table 3.

Medium. Antifungal susceptibility testing was performed with RPMI 1640 medium (Sigma Chemical Co., St. Louis, Mo.) with glutamine, but without sodium bicarbonate and buffered at pH 7.0 with 0.165 M morpholinopropanesulfonic acid.

Antifungal in vitro susceptibility testing. Experiments for determination of MICs of yeasts were performed by the broth macrodilution method according to the recommendations of the National Committee for Clinical Laboratory Standards. See *National Committee for Clinical Laboratory Standards. Reference method for broth dilution susceptibility testing of yeasts Document M27-T.* Tentative standard, National Committee for Clinical Laboratory Standards, Wayne, Pa., 1995). The only difference compared to the standardized method was the choice of drug dilutions, which ranged from 100 to 0.09 μg/ml. Briefly, this method specifies the use of an inoculum grown at 35° C. and adjusted to a concentration of 0.5×10$^3$ to 2.5×10$^3$ CFU/ml, incubation of the culture at 35° C., and reading at 48 h for all yeasts except for *C. neoformans*, for which the results are interpreted at 72 h. The MIC was defined as the culture with the lowest drug concentration in which a visual turbidity less than or equal to 80% inhibition compared to that produced by the growth control tube was observed.

The minimum fungicidal concentration (MFC) was determined by plating 100 μl aliquots from tubes showing complete inhibition of growth on Sabouraud agar plates. The lowest drug concentration that yielded three or fewer colonies was recorded as the MFC.

Molds were tested by the same method but with the following modifications. Isolates were grown on Sabouraud dextrose agar at 30° C., after adequate sporulation occurred (4 to 14 days); conidia were harvested by flooding the colonies with a sterile solution of 0.85% NaCl and 0.05% Tween 80 in sterile distilled water. Inocula were prepared with a hemocytometer for counting and were then diluted with RPM1 1640 medium to obtain a final inoculum size of approximately 0.5×10$^3$ to 2.5×10$^3$ CFU/ml. The inoculum size was verified by plating an aliquot of the inoculum. The cultures were incubated at 30° C. for 48 to 72 h or until growth in the control tube was visible.

EXAMPLE 12

Results of Biological Testing

Melting temperatures were measured for the compounds 5 and 6 bound to poly dA.dT to obtain a qualitative evaluation of the DNA binding affinity of these drug candidates (Table 2). The difference in Tm values between the drug-DNA complexes and free DNA in solution (ΔTm) provides a useful tool to assess the interaction strength of the molecules with DNA. Since several of the compounds bound very strongly to poly dA.dT (Table 2), the interaction of these compounds with the Dickerson-Drew dodecamer d (CGCGAATTCGCG)$_2$ (SEQ ID NO:1), a DNA with a different and shorter AT sequence and different groove characteristics, was also studied. The reduced binding of the drugs to the dodecamer reflected by the lower ΔTm values of the drug-dodecamer complexes (Table 2), allowed for a better relative comparison of the DNA binding affinity of these putative minor-groove binding compounds.

different base pair selectivity for the two structurally closely related dicationic analogs. However, introduction of a methyl group on each of the two phenyl rings of the 2,5-diarylfuran system with a terminal phenyl group, 6g, resulted in lowering of the ΔTm value to one similar to that of its pyridyl counterpart, 6h. The use of small alkyl terminal groups, methyl groups as found in 6e and 6f, also led to a significant drop in binding affinity.

The placement of a single substituent on each of the two phenyl rings of the 2,5-diarylfuran framework produced striking differences in ΔTm values for both the diguanidine and reversed amidine series. Again, based on the comparison of ΔTm values for binding to the dodecamer for the diguanidine series, it is noted that placement of single substituent of

TABLE 2

In vitro Antimicrobial Activities and DNA binding results for inventive compounds.

| Comp. No. | C. albicans | | Aspergillus fumigatus | | | MTb | DNA Affinities[b] | |
|---|---|---|---|---|---|---|---|---|
| | MIC (μg/ml) | MFC (μg/ml) | MIC (μg/ml) | MFC (μg/ml) | % Inh[a] | MIC (μg/ml) | ΔTm (AT) | ΔTm (oligo) |
| 5a | 12.5 | 25 | 100 | >100 | | 3.13 | 21.6 | 10.8 |
| 6a | Nt | nt | nt | nt | | 1.56 | 19.6 | 7.5 |
| 6b | 25 | 50 | nt | nt | | 1.56 | 28.6 | 15.0 |
| 6c | >100 | nt | nt | nt | | ≦6.25 | >28 | 15.4 |
| 6d | >100 | nt | 100 | >100 | | ≦6.25 | 26.7 | 12.8 |
| 6e | >100 | nt | 100 | >100 | 0 | nd | 15.9 | 6.0 |
| 6f | >100 | nt | >100 | nt | 18 | nd | 14.5 | 2.4 |
| 5b | 1.04 | 2.08 | 33.4 | 33.4 | | ≦1 | 17.8 | 6.9 |
| 5c | 10 | 100 | 100 | 100 | | 16 | 15.2 | 2.8 |
| 5d | 10 | 100 | 100 | 100 | | 4 | 26.1 | 4.7 |
| 5e | 10 | 10 | 100 | 100 | | 8 | 5.9 | 0 |
| 5f | Nt | nt | nt | nt | | | 2.7 | 1.4 |
| 6g | 3.12 | 6.25 | nt | nt | | 3.13 | 24.9 | 7.8 |
| 6h | 10 | 10 | 10 | 100 | | ≦1 | 22.6 | 8.9 |
| 6i | 100 | 100 | 100 | nt | | | 7.5 | 1.1 |
| 6j | ≦1 | 10 | 10 | nt | | 2 | 24.3 | 10.8 |
| 6k | ≦1 | ≦1 | ≦1 | ≦1 | | ≦1 | 19.0 | 7.8 |
| 6l | 100 | >100 | >100 | nt | | 8 | 5.2 | 0 |
| 6m | 10 | >100 | 10 | >100 | | | 5.7 | 1.2 |
| DB 686 | 4.17 | 4.17 | | | | <1 | | |
| DB 653 | >100 | | >100 | | | | 20.2 | 12.8 |

[a] % Inhibition at 6.25 μg/ml
[b] AT = poly dA.dT; oligo = d(CGCGAATTCGCG)$_2$
c nt = not tested
d nd = not determined The parent diguanidino compound 5a showed a strong affinity for DNA as judged by the ΔTm values for both poly dA.dT (21.6) and the dodecamer (10.8). These values compare well to those (25 and 11.7) for the parent amidine 2,5-bis [4-amidinophenyl]furan suggesting little difference in affinities in this core furan structure for the amidine and guanidine cationic centers. Based on the comparison of ΔTm values for binding to the dodecamer for the parent diguanidino 5a and for the various reversed amidine congeners 6a–6e, several interesting effects resulting from structural variation of the terminal groups are noted. First, reversed amidines bearing phenyl, substituted phenyl or cyclohexyl terminal groups (6b, 6c and 6d) showed an increase in affinity over that of the parent diguanidino 5a. In a related series of diamidines, such an increase in affinity with increasing bulk of terminal groups was attributed to increased van der Waals interactions of the terminal groups with the walls of the minor-groove and such is likely the case in this system. Interestingly, the ΔTm value for the compound with a terminal 2-pyridyl group 6a is significantly lower than that for its phenyl counterpart 6b. The lower affinity of 6a may suggest a different binding mode or roughly the same size but of differing electronic properties on the phenyl rings resulted in a lowering of the ΔTm values; compare the values of 5a with 5b–5e. The most dramatic effect was observed for the strongest electron-withdrawing group, the CF$_3$ of 5e, which reduced the ΔTm value to zero.

The ΔTm values for a series of compounds with terminal 2-pyridyl groups (6a, 6h–6m) showed a different sensitivity to substituents. In this case, the introduction of a single substituent on each of the two phenyl rings of the 2,5-diarylfuran framework caused little effect on the ΔTm values when the substituent was methyl (6h) or methoxy (6k). However, introduction of a chloro group (6l) resulted in significant reduction of the value, perhaps in part due to a pK effect. The detrimental effect of the chloro group on the ΔTm was much greater for the pyridyl derivative 6l than for the analogous guanidine 5d, possibly due to the lower basicity of the reversed amidine in comparison to the guanidine. In agreement with the results from the diguanidine series, the introduction of two methyl groups on each of the core phenyl rings (6m) also dramatically reduced the DNA affinity. Interestingly, replacement of the terminal 2-pryridyl with a 2-quinoyl group (6I) also resulted in a significant reduction of the ΔTm suggesting definite limits on the dimensions of the terminal group. On the other hand, the introduction of a methyl group on the terminal pyridyl ring (6j) slightly enhanced the binding affinity.

The antimicrobial data for these compounds are also summarized in Table 2. The greatest activity amongst the diguanidino compounds was found for 5a and 5b, which showed good in vitro activity against both *Candida albicans* and *Mycobacterium tuberculosis*. These compounds gave MIC values between 1 to 3 μg/ml against both organisms. Both compounds were fungicidal against *C. albicans*. The 2,5-bis [alkylimino]aminophenyl]furans (6d, 6e, 6f), in general, did not show significant antimicrobial activity, although compound 6d, with the larger cyclohexyl group, did exhibit some activity against *M. tuberculosis*.

The 2,5-bis [arylimino]aminophenyl]furans can be divided into two groups: those in which the terminal group is phenyl or substituted phenyl and those in which it is 2-pyridyl or substituted 2-pyridyl. The terminal phenyl group class of compounds did not exhibit high antifungal activity; however, both 6b and 6g did show significant activity against *M. tuberculosis* with MIC values of 0.78 and 1.56 μg/ml, respectively. Four of the compounds in the terminal pyridyl group class (6a, 6h, 6j and 6k) showed promising activity against *M. tuberculosis* with MIC values ranging from 1.0 to 2.0 μg/ml. Most of the 2-pyridyl compounds exhibited only moderate antifungal activity. As exceptions, 6j and 6k showed activity at the MIC level of ≦1.0 μg/ml against *C. albicans*, and 6k showed a similar level of activity against *Aspergillus fumigatus*.

In order to evaluate the spectrum of antifungal activity of these compounds, pyridyl-substituted amidines 6j and 6k were selected for studies against other pathogenic fungi (Table 3). Compound 6j was quite effective against *C. albicans* and exhibited fungicidal activity against several strains. Compound 6j was less effective versus both Aspergillus species. Compound 6j showed good fungicidal activity versus *Rhizopus arrhizus*; however, it was not very effective against the mold *Fusarium solani*. Compound 6k did not show significant activity in the expanded fungus panel.

To summarize, dicationic 2,5-bis (4-guanidinophenyl) furans 5a–5f, 2,5-bis [4-(arylimino)aminophenyl]furans 6a–6c, 6g–6m, and 2,5-bis [4-(alkylimino)aminophenyl] furans 6d–6f have been synthesized starting from 2,5-bis [tri-n-butylstannyl]furan. Thermal melting studies with poly dA.dT and the duplex oligomer d(CGCGAATTCGCG)$_2$ (SEQ ID NO: 1) demonstrated high DNA binding affinities for a number of the compounds. Both the guanidines and the reversed amidines in the 2,5-diarylfuran series have strong DNA binding properties.

Compounds in both these classes show both antifungal and anti-mycobacterial activity. In addition, they may be broad-spectrum anti-fungal agents. Of the nineteen novel dicationic compounds synthesized, six (6a, 6b, 5b, 6h, 6j, 6k) exhibited MICs of 2 μg/ml or less versus *Mycobacterium tuberculosis*. Of the nineteen screened against *Candida albicans*, four gave MICs of 2 μg/ml or less (5a, 5b, 6j, 6k) and two (5a, 6k) were fungicidal, unlike a standard antifungal drug Fluconazole which was fungistatic. One of the tested compounds (6k) exhibited a MIC of 1 μg/ml and was also fungicidal for *Aspergillus fumigatus*. Some compounds possessed inhibitory activity against *Cryptococcus neoformans* but all appeared less potent for this pathogenic yeast compared with *C. albicans* and *A. fumigatus*.

Evaluation against *Trypanosoma brucei rhodesiense* in vitro showed that the (arylimino)aminophenyl furans, especially when aryl is 2-pyridyl, were effective in the 0.02 to 0.1 μg/mL range; approximately 1/10 as effective as pentamidine and furamidine. In contrast, these new compounds are ten times more effective than pentamidine and furamidine, and comparable in activity to benznidazole, against *T. cruzi*.

TABLE 3

Evaluation of Compound 6j against an Expanded Fungus Panel

| Genus, species, isolate number | MIC 80% | MIC 100% | MFC |
|---|---|---|---|
| *Aspergillus flavus* 194.99 | 3.12 | 6.25 | >100 |
| *Aspergillus flavus* 107.96 | 3.12 | 50 | >100 |
| *Aspergillus flavus* 141.88 | 3.12 | 50 | >100 |
| *Aspergillus fumigatus* 168.95 | 50 | 50 | >100 |
| *Aspergillus fumigatus* 182.99 | 3.12 | 50 | >100 |
| *Aspergillus fumigatus* 119.00 | 3.12 | 50 | >100 |
| *Aspergillus fumigatus* 165.86 | 50 | 50 | >100 |
| *Aspergillus fumigatus* 153.90 | 3.12 | 50 | >100 |
| *Fusarium solani* 152.89 | 3.12 | 50 | 50 |
| *Rhizopus arrhizus* 117.89 | 0.78 | 1.56 | 1.56 |
| *Candida albicans* 116.98 | 1.56 | 1.56 | >100 |
| *Candida albicans* 159.95 | 0.79 | 1.58 | 3.12 |
| *Candida albicans* 149.97 | 0.78 | 1.56 | 6.25 |
| *Candida albicans* 156.97 | 1.56 | 3.15 | >100 |
| *Candida albicans* 126.97 | 1.56 | 3.12 | 3.12 |
| *Candida albicans* 117.00 | 0.78 | 3.12 | 25 |
| *Candida albicans* A39 | 1.56 | 1.56 | 25 |
| *Cryptococcus neoformans* H99 | 1.56 | 1.56 | >100 |

MIC and MFC values are μg/ml.
MIC 80% = 80% of inoculum is inhibited.
MIC 100% = 100% of inoculum is inhibited.
MFC = minimum fungicidal concentration.

In the specification, and examples there have been disclosed typical preferred embodiments of the invention and, although specific terms are employed, they are used in a generic and descriptive sense only and not for the purposes of limitation, the scope of the invention being set forth in the following claims.

That which is claimed is:

1. A compound according to Formula I:

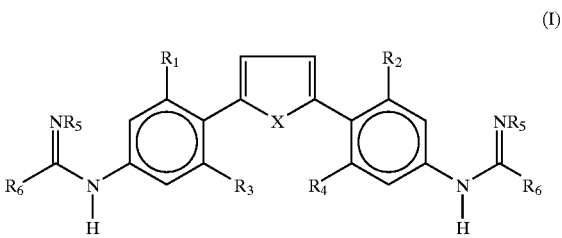

(I)

wherein:
  $R_1$, $R_2$, $R_3$ and $R_4$ are each independently selected from the group consisting of H, alkyl, alkoxy, halide, and alkylhalide groups;
  $R_5$ is H or alkyl;
  $R_6$ is H, alkyl, or $NR_7R_8$, wherein $R_7$ and $R_8$ are each independently selected from the group consisting of H and alkyl; and
  X is O.

2. The compound according to claim 1, wherein $R_1$ and $R_2$ are each H.

3. The compound according to claim 1, wherein $R_1$ and $R_2$ are each H and $R_3$ and $R_4$ are each lower alkyls.

4. The compound according to claim 1, wherein $R_3$ and $R_4$ are each a halide.

5. The compound according to claim 1, wherein $R_3$ and $R_4$ are each alkoxy.

6. The compound according to claim 1, wherein $R_3$ and $R_4$ are each alkyl halides.

7. The compound according to claim 1, wherein $R_5$ is H, $R_6$ is a $NR_7R_8$, and $R_7$ and $R_8$ are each an H.

8. A pharmaceutical composition comprising a compound according to Formula I:

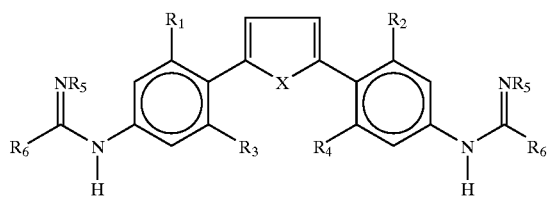

(I)

wherein:
- $R_1$, $R_2$, $R_3$ and $R_4$ are each independently selected from the group consisting of H, alkyl, alkoxy, halide, and alkylhalide groups;
- $R_5$ is H or alkyl;
- $R_6$ is H, alkyl, or $NR_7R_8$, wherein $R_7$ and $R_8$ are each independently selected from the group consisting of H and alkyl; and
- X is O;

in a pharmaceutically acceptable carrier.

9. The pharmaceutical composition of claim 8, wherein the composition is formulated for parenteral administration.

10. The pharmaceutical composition of claim 8, wherein the composition is formulated for oral administration.

11. The pharmaceutical composition of claim 8, wherein the composition is formulated for topical administration.

12. A process for preparing a pharmaceutical composition comprising admixing the compound of the formula (I) according to claim 1 and optionally a pharmaceutically utilizable carrier.

13. A method of treating an microbial infection in a subject in need of such treatment, wherein the microbial infection is caused by a microorganism selected from the group consisting of *Mycobacterium tuberculosis,* Trypanosoma spp., *Candida albicans,* Aspergillus spp., *Cryptosporidium parvum, Giardia lamblia,* Plasmodium spp., *Pneumocystis carinii, Toxoplasma gondii, Fusarium solani,* and *Cryptococcus neoformans,* said method comprising administering to the subject a compound according to Formula I or a pharmaceutically acceptable salt thereof:

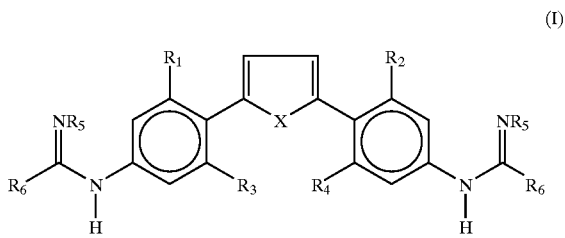

(I)

wherein:
wherein $R_1$, $R_2$, $R_3$ and $R_4$ are each independently selected from the group consisting of H, alkyl, alkoxy, halide, and alkylhalide groups;

$R_5$ is H or alkyl;

$R_6$ is H, alkyl, or $NR_7R_8$, wherein $R_7$ and $R_8$ are each independently selected from the group consisting of H and alkyl; and X is O.

14. The method according to claim 13, wherein the compound is administered parenterally.

15. The method according to claim 13, wherein the compound is administered orally.

16. The method according to claim 13, wherein the compound is administered topically.

* * * * *

UNITED STATES PATENT AND TRADEMARK OFFICE
CERTIFICATE OF CORRECTION

PATENT NO.       : 6,737,440 B2                                              Page 1 of 1
APPLICATION NO.  : 10/008535
DATED            : May 18, 2004
INVENTOR(S)      : Boykin et al.

It is certified that error appears in the above-identified patent and that said Letters Patent is hereby corrected as shown below:

On title page, item 75 Inventors
replace "Chad F. Stephens"
with --Chad E. Stephens--.

Signed and Sealed this

Twenty-sixth Day of October, 2010

David J. Kappos
*Director of the United States Patent and Trademark Office*